United States Patent [19]

Algieri et al.

[11] Patent Number: 4,927,968
[45] Date of Patent: May 22, 1990

[54] CHEMICAL INTERMEDIATES AND PROCESS

[75] Inventors: Aldo A. Algieri, Killingworth, Conn.; Robert F. Farney, Evansville, Ind.

[73] Assignee: Bristol-Myers Company, New York, N.Y.

[21] Appl. No.: 174,444

[22] Filed: Apr. 11, 1988

Related U.S. Application Data

[63] Continuation-in-part of Ser. No. 50,459, May 14, 1987, abandoned.

[51] Int. Cl.$^5$ .............................................. C07C 93/06
[52] U.S. Cl. ..................... 549/451; 564/306
[58] Field of Search ........................ 564/354, 353, 653

[56] References Cited

U.S. PATENT DOCUMENTS

| | | | |
|---|---|---|---|
| 4,390,701 | 6/1983 | Algieri et al. | 546/235 |
| 4,395,553 | 7/1983 | Algieri et al. | 546/235 |
| 4,521,625 | 6/1985 | Brown et al. | 564/461 |
| 4,522,943 | 6/1985 | Algieri et al. | 514/183 |
| 4,526,973 | 7/1985 | Algieri et al. | 546/235 |

FOREIGN PATENT DOCUMENTS 2023133 4/1979 United Kingdom .

*Primary Examiner*—John Kight, III
*Assistant Examiner*—Nathan M. Nutter
*Attorney, Agent, or Firm*—Aldo A. Algieri

[57] ABSTRACT

The present invention relates to novel intermediates of the formula

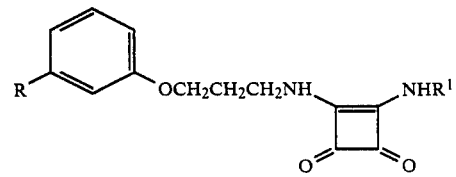

wherein $R^1$ is hydrogen or lower alkyl and R is

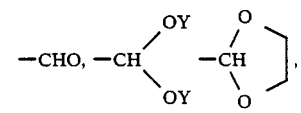

—CH$_2$OH or —CH$_2$X in which X is a conventional leaving group and Y is lower alkyl and the use thereof in a process for the preparation of certain histamine H$_2$-antagonists.

5 Claims, No Drawings

CHEMICAL INTERMEDIATES AND PROCESS

CROSS-REFERENCE TO RELATED APPLICATION

This application is a continuation-in-part of our prior, co-pending application Ser. No. 050,459 filed May 14, 1987 and now abandoned.

BACKGROUND OF THE INVENTION

1. Field of the Invention

The present invention provides novel intermediates and their use in the preparation of certain histamine $H_2$-antagonists which are useful in the treatment of peptic ulcers and other conditions caused or exacerbated by gastric acidity.

2. Disclosure Statement

Our colleagues A. A. Algieri and R. R. Crenshaw disclose histamine $H_2$-receptor antagonists in U.S. Pat. Nos. 4,390,701 issued June 28, 1983, 4,395,553 issued July 26, 1983, 4,522,943 issued June 11, 1985 and 4,526,973 issued July 2, 1985 which are substantially the same as those described by the present invention.

U.S. Pat. No. 4,521,625 issued June 4, 1985 to T. H. Brown and R. C. Young discloses intermediates of the formula

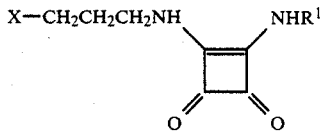

wherein $R^1$ is hydrogen or a $C_{1-6}$ alkyl group and X is hydroxy or a group displaceable by hydroxy or the equivalent thereof which are used in a process for the preparation of compounds which are substantially the same as those described in the above-mentioned U.S. patents.

United Kingdom patent application GB No. 2,023,133 published Dec. 28, 1979 discloses inter alia intermediates of the formula

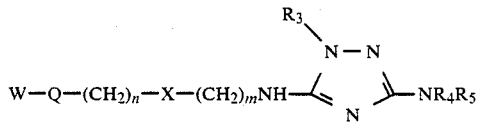

in which W represents the group —CHO or —$(CH_2)_p CONR_1R_2$ and Q, n, X, m, $R_3$, $R_4$, $R_5$, $R_1$ and $R_2$ correspond to a large number of substituents.

The novel intermediates provided in the present invention are useful in an improved process for the preparation of histamine $H_2$-antagonists described herein.

SUMMARY OF THE INVENTION

Histamine $H_2$-receptor antagonists of the formula

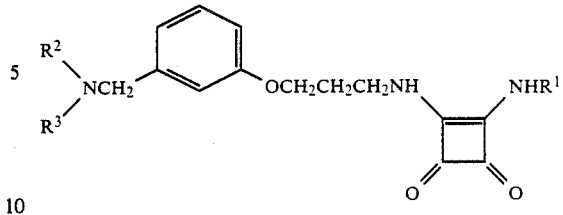

wherein $R^1$ is hydrogen or lower alkyl and $R^2$ and $R^3$ are as defined below, which are useful in treating peptic ulcers, are prepared via a new process from novel intermediates of the formula

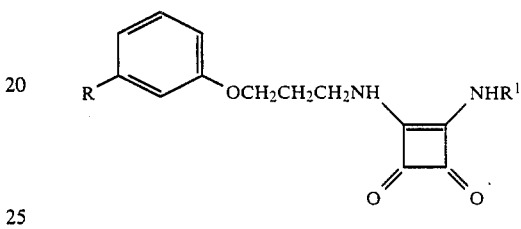

wherein $R^1$ is hydrogen or lower alkyl and R is

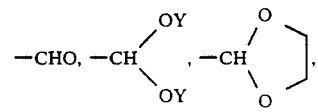

—$CH_2OH$ or —$CH_2X$ in which X is a conventional leaving group and Y is lower alkyl.

DESCRIPTION OF THE INVENTION

The present invention relates to novel intermediates which are useful in the preparation of certain histamine $H_2$-antagonists which are described herein. Accordingly, the present invention provides compounds of the formula

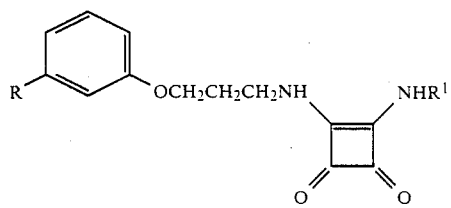

wherein $R^1$ is hydrogen or lower alkyl and R is

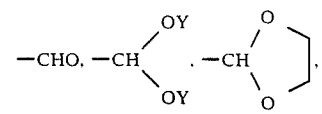

—$CH_2OH$ or —$CH_2X$ in which X is a conventional leaving group and Y is lower alkyl.

Preferably $R^1$ is hydrogen and R is —CHO, or —$CH_2X$ in which X is a conventional leaving group. Suitable conventional leaving groups are well-known to those skilled in the art. Preferably X is bromo, iodo, chloro or —$O_3SR^4$ in which $R^4$ is lower alkyl, trifluoromethyl, phenyl or substituted phenyl. Most preferably R is —CHO.

In the present invention, as used herein and in the claims, the term "lower alkyl" means straight or branched chain alkyl containing from 1 to 6 carbon atoms. Preferably they contain from 1 to 4 atoms and, most preferably, they contain 1 to 2 carbon atoms. Unless otherwise specified in the particular instance, the terms "butyl" and "butoxy" as used herein and in the claims is intended to mean n-butyl and n-butoxy. The use of the terms "butyl" and "butoxy" are only a convenience and are not intended to exclude other $C_4$ alkyl groups from the scope of the present invention.

The compounds of formula IV may be prepared from the compound of formula II by reaction with a compound of formula III. The acetal of formula Ia thereby produced is hydrolyzed to an aldehyde of formula Ib followed by reaction with a secondary amine in the presence of formic acid to produce the desired histamine $H_2$-antagonist of the formula IV as illustrated in Scheme 1.

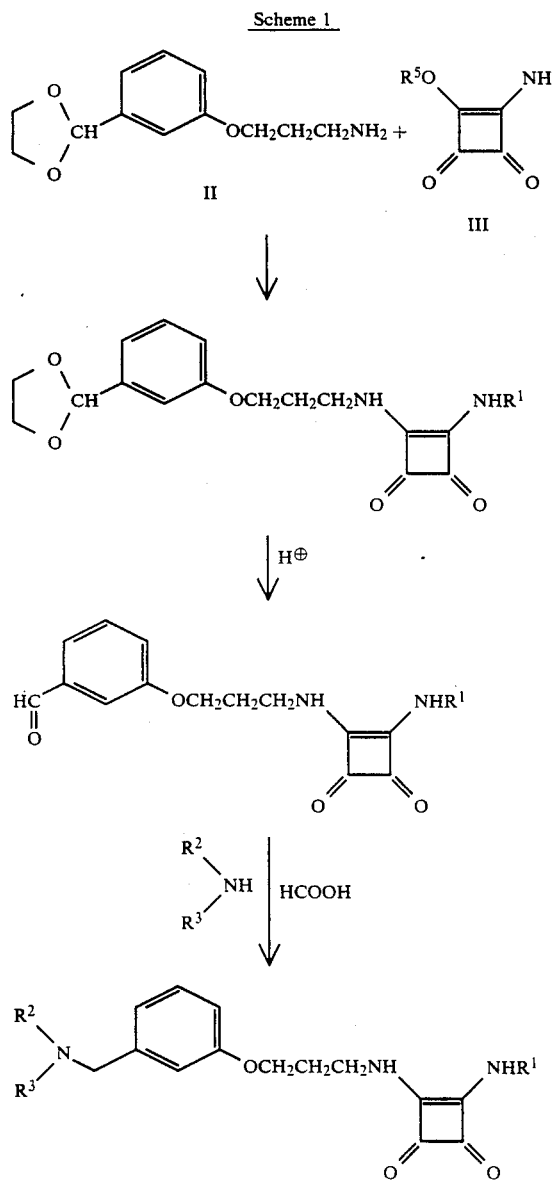

The compound of formula II may be prepared as described in the present invention or by procedures described in United Kingdom patent application GB No. 2,023,133 published Dec. 28, 1979.

The compounds of formula III may be prepared by the reaction of ammonia or a primary lower alkyl amine with a 1,2-dialkoxy-1-cyclobutene-3,4-dione which is itself prepared from squaric acid according to the general procedures described by G. Maahs, *Justus Liebigs Ann. Chem.* 686, 55 (1965) and A. H. Schmidt, *Synthesis,* 869 (1978). The compounds of formula III may be prepared in a two-step process from squaric acid, however, in another aspect of the present invention, we have found that the novel compound of formula III wherein $R^1$ is hydrogen and $R^5$ is butyl may be prepared in a stepwise manner in a "one pot" reaction. Furthermore, we have found that the preferred 1-amino-2-butoxy-1-cyclobutene-3,4-dione as described herein may readily be prepared in high yield and purity on a manufacturing scale in a "one pot" reaction from squaric acid which is especially useful for the preparation of the compounds of the present invention and certain histamine $H_2$-antagonists thereof.

In reaction Scheme 1, $R^1$ is hydrogen or lower alkyl and, preferably, hydrogen. Preferably $R^5$ is cyclohexyl or lower alkyl for example, methyl, ethyl, propyl, isopropyl, butyl, sec-butyl, tertiary-butyl, neopentyl, pentyl and the like. Most preferably, $R^5$ is butyl, sec-butyl or neopentyl. For the compounds of formula IV or a non-toxic pharmaceutically acceptable salt thereof, $R^2$ and $R^3$ are lower alkyl, or $R^2$ and $R^3$, taken together with the nitrogen to which they are attached, may be pyrrolidino, methylpyrrolidino, piperidino, methylpiperidino, homopiperidino, heptamethyleneimino or octamethyleneimino. Most preferably, $R^2$ and $R^3$ are joined together with the nitrogen atom to form a piperidino group.

The compounds of formula Ia may be prepared by the reaction of the compound of formula II with a compound of formula III in a non-reactive solvent such as methanol, ethanol, acetonitrile, tetrahydrofuran and the like at a temperature from about 0° C. to the reflux temperature of the solvent. For convenience, we prefer to conduct the reaction at about ambient temperature.

The aldehydes of the formula Ib may be prepared by acid hydrolysis of the acetals of formula Ia. The hydrolysis reaction may be conducted in a non-reactive solvent such as methanol, ethanol, tetrahydrofuran and aqueous mixtures thereof in the presence of an organic or inorganic acid for example, hydrochloric acid, sulfuric acid, formic acid and p-toluenesulfonic acid.

The histamine $H_2$-antagonist compounds of formula IV may then be prepared by the reaction of a compound of formula Ib with a secondary amine of the formula $R^2R^3NH$ in the presence of at least one equivalent of formic acid as reducing agent. The reductive amination may be conducted in an excess of formic acid wherein the formic acid is also used as solvent. Preferably the reaction is conducted in a non-reactive solvent such as benzene, toluene, xylene and n-propanol with at least one equivalent of formic acid and, preferably, two to three equivalents. It is also preferred to azeotropically remove the water which is thereby produced at about the reflux temperature of the solvent employed.

The compounds of formula IV may also be prepared from the compounds of formula Ib as illustrated in Scheme 2.

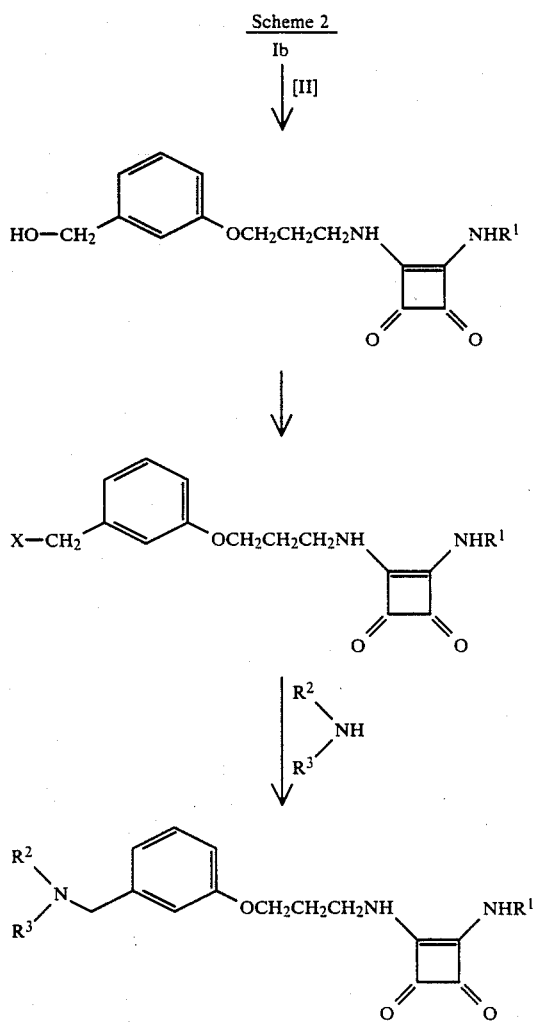

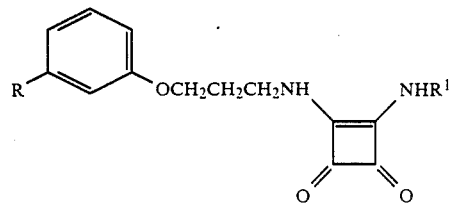

with a compound of the formula

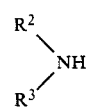

wherein R, $R^1$, $R^2$ and $R^3$ are as previously defined in the presence of at least one equivalent of formic acid until substantially the compound of formula IV is produced.

In a preferred embodiment, the process is carried out in a non-reactive solvent in the presence of at least one equivalent of formic acid and, more preferably two to three equivalents of formic acid.

DESCRIPTION OF SPECIFIC EMBODIMENTS

In the following examples, all temperatures are given in degrees Centigrade and melting points and boiling points are uncorrected. All evaporations of solvents were performed under reduced pressure. As used herein, the term Skellysolve B is a petroleum solvent fraction having a bp range of 60°–80° C. consisting essentially of n-hexane.

EXAMPLE 1

1-Amino-2-butoxy-1-cyclobutene-3,4-dione

Preparation A: A solution of 1,2-dibutoxy-1-cyclobutene-3,4-dione (6.09, 0.027 mole) in 40 mL of tetrahydrofuran was cooled to 5° C. in an ice-water bath and treated dropwise over a period of 9 minutes with a solution of 1.8 mL of concentrated ammonium hydroxide in a mixture of 8 mL of tetrahydrofuran and 1 mL of methanol. After stirring at 5° C. for 30 minutes and at ambient temperature for 90 minutes the mixture was concentrated under reduced pressure to a slurry. A small amount of Skellysolve B was added and the product was collected by filtration after 16 hours of standing at 0° C. to give 3.26 g of the title compound. A sample (8.54 g) was partly dissolved in acetone, filtered and cooled to give 4.51 g of purified title compound; mp=165.5°–168° C. (clear melt).

Anal. Calcd. for $C_8H_{11}NO_3$: C, 56.79; H, 6.56; N, 8.28. Found: C, 56.46; H, 6.19; N, 8.56.

In reaction Scheme 2, a compound of formula Ib is reduced to an alcohol of formula Ic which is then converted by conventional techniques to a compound of formula Id. The conventional leaving group is then displaced by an amine of the formula $R^2R^3NH$ to produce the desired histamine H$_2$-antagonist of the formula IV wherein $R^1$, $R^2$ and $R^3$ are as previously defined.

The compounds of formula Ic may be prepared from the aldehydes of formula Ib by catalytic hydrogenation or reducing metal hydrides according to methods well-known in the art. The conversion of the hydroxy radical in formula Ic to a conventional leaving group may be carried out with suitable halogenating agents or sulfonating agents. Suitable halogenating agents such as thionyl chloride and thionyl bromide may be employed neat or in a non-reactive solvent and, preferably, in the presence of a base such as a tertiary amine (e.g., triethylamine, pyridine and lutidine) or inorganic base (e.g., sodium carbonate and potassium carbonate) at a temperature of 0° C. to about the reflux temperature of the solvent. Suitable sulfonating agents such as methanesulfonyl chloride, benzenesulfonyl chloride, p-toluenesulfonyl chloride, p-bromobenzenesulfonyl chloride and p-nitrobenzenesulfonyl chloride may be employed in a non-reactive solvent, for example, dichloromethane, acetonitrile, tetrahydrofuran, and dimethylformamide and, preferably, in the presence of a tertiary amine or inorganic base to remove the acid which is produced.

The compounds of formula IV may then be prepared by the reaction of a compound of formula Id with the appropriate amine of formula $R^2R^3NH$ in a non-reactive solvent and preferably in the presence of a base to remove the acid which is thereby produced.

In another aspect, the present invention provides a process for the preparation of histamine H$_2$-antagonists of the formula IV comprising the step of reacting a compound of the formula Preparation B: A solution of 1,2-dibutoxy-1-cyclobutene-3,4-dione (30.0 g, 0.123 mole, 92.5 area % pure by glc assay) in 300 mL of tetrahydrofuran was cooled to 5° C. and treated dropwise, over 30 minutes, with a solution of concentrated NH$_4$OH (8.18 mL, 0.123 mole) in a mixture of 40 mL of tetrahydrofuran and 5 mL of methanol. The resultant solution was stirred in the ice-water bath for 30 minutes followed by 5.5 hours at ambient temperature.

The hazy solution was filtered through diatomaceous earth to remove a small amount of bright yellow solid and the filtrate was concentrated under reduced pressure to near dryness. The solid residue was rubbed under a small amount of Skellysolve B and diethyl ether and cooled at 0° C. The mixture was filtered and dried to give 17.9 g (86%) of the title compound as white solid; mp=165°-167.5° C. (clear melt).

Preparation C: In a 5-Liter flask equipped with stirrer and nitrogen inlet/outlet tubes was placed 1,2-dihydroxy-1-cyclobutene-3,4-dione (400.0 g, 3.506 moles), 1-butanol (1.2 L) and toluene (800 mL). The mixture was stirred and heated under reflux with a Dean-Stark water trap until water stopped passing over (136 mL water collected, about 5.5 hours). The clear reaction mixture was heated under reflux for a further one hour, then cooled under nitrogen to 0°-5° C. The cooled stirred solution was treated dropwise at such a rate that the reaction remains at or below 10° C. (2.5 hours required) with a solution containing 14M ammonium hydroxide (240 mL, 3.37 moles), 1-butanol (960 mL) and methanol (40 mL). Stirring was continued at ambient temperature for 2 hours, then the mixture was cooled to 0°-5° C. for 1.5 hours and filtered. The product was washed with toluene (800 mL) and dried to give 492.4 g (88.0%) of the title compound; mp=165°-168° C.

EXAMPLE 2

N-[3-(3-Formylphenoxy)propyl]phthalimide

Method A. A mixture of 3-hydroxybenzaldehyde (183.2 g, 1.5 moles), 1-bromo-3-chloropropane (167 mL, 1.58 moles), potassium carbonate (450 g) and acetonitrile (2.2 L) was heated at reflux temperature with good stirring. After 17 hours, the reaction mixture was cooled to ambient temperature and filtered. The filtrate was evaporated under reduced pressure and the residue was dried in vacuo to give 290.4 g (97%) of 1-(3-formylphenoxy)-3-chloropropane.

A mixture of 1-(3-formylphenoxy)-3-chloropropane (207.1 g, 1.04 moles), phthalimide (161.0 g, 1.09 moles), tetrabutylammonium bromide (16.8 g, 0.052 mole) and potassium carbonate (200 g, 1.45 moles) in dimethylformamide (1.1 L) and water (14 L) and slowly heated to 65° C. After 24 hours, the mixture was poured into 14 L of water and resulting mixture was stirred for 2 hours, filtered and dried in vacuo to give 285 g of product. Recrystallization from 2-propanol yield 273.7 g (85% overall yield) of title compound, mp=102°-103° C.

Method B. A mixture of 3-hydroxybenzaldehyde (d32.5 g, 266 mmole), N-(3-bromopropyl)phthalimide (71.5 g, 267 mmole) and potassium carbonate (40.38 g, 293 mmole) in 700 mL of dimethylformamide was stirred at ambient temperature. After 18 hours, the mixture was diluted with 2 L of water, filtered and dried to yield 67 g of title compound.

EXAMPLE 3

N-{3-[3-(1,3-dioxolan-2-yl)phenoxy]propyl}phthalimide

To a solution of N-[3-(3-formylphenoxy)propyl]phthalimide (92.8 g, 0.3 mole), ethylene glycol (44 mL, 0.8 mole) in benzene (1.5 L) was added 3 g of p-toluenesulfonic acid and the mixture was refluxed under a Dean-Stark trap for 14 hours. The cooled mixture was extracted with 100 mL of saturated aqueous sodium bicarbonate and then with 200 mL of saturated aqueous sodium chloride. The organic phase was dried and evaporated under reduced pressure to give 119.4 g of the title compound which crystallized on standing.

EXAMPLE 4

3-[3-(1,3-Dioxolan-2-yl)phenoxy]propylamine

A solution of N-{3-[3-(1,3-dioxolan-2-yl)phenoxy]propyl}phthalimide (119.4 g, 0.3 mole) and hydrazine hydrate (78.6 mL, 1.62 mole) in 95% ethyl alcohol (1.5 L) was heated at reflux temperature for 17.5 hours. The thick white mixture was cooled in an ice-water bath, filtered and the solid washed with ice cold 95% ethyl alcohol. The combined filtrate and washings were evaporated under reduced pressure and the residue was partitioned between 940 mL of 5% aqueous sodium hydroxide and 500 mL of dichloromethane. The aqueous phase was extracted with 500 mL of dichloromethane and the combined organic phase was extracted with 300 mL of saturated aqueous sodium chloride. The organic phase was dried, evaporated under reduced pressure and the residue was distilled under high vacuum to give 49.9 g of the title compound; bp=143°-147° C. at 0.25 mmHg.

EXAMPLE 5

1-Amino-2-{3-[3-(1,3-dioxolan-2-yl)phenoxy]propylamino}-1-cyclobutene-3,4-dione

A solution of 3-[3-(1,3-dioxolan-2-yl)phenoxy]propylamine (12.62 g, 56.5 mmole) and 1-amino-2-butoxy-1-cyclobutene-3,4-dione (10.0 g, 56.5 mmole) in 250 mL of methanol was stirred at ambient temperature. After 21 hours, the thick reaction mixture was filtered and the filter cake was washed with cold methanol. The collected solid was dried in vacuo to give 17.9 g of the title compound.

A 1.5 g sample was recrystallized from absolute ethanol to give 1.33 g of purified title compound; mp=209°-210.5° C.

Anal. Calcd for $C_{16}H_{18}N_2O_5$: C, 60.37; H, 5.70; N, 8.80. Found: C, 60.71; H, 5.70; N, 8.63.

EXAMPLE 6

1-Amino-2-[3-(3-formylphenoxy)propylamino]-1-cyclobutene-3,4-dione

The 1-amino-2-{3-[3-(1,3-dioxolan-2-yl)phenoxy]propylamino}-1-cyclobutene-3,4-dione (11.66 g, 0.037 mole) was suspended in a solution of 200 mL of 95% ethanol and 20 mL of aqueous 2.0N HCl. The suspension was stirred at ambient temperature for 2 hours, then filtered (slowly) and dried in vacuo to give 9.85 g of crude title compound. Recrystallization from 150 mL of 95% ethanol and 35 mL of aqueous 1N HCl yielded 5.74 g of purified title compound; mp=203°-206° C.

Anal. Calcd for $C_{14}H_{14}N_2O_4$: C, 61.30; H, 5.14; N, 10.22. Found: C, 61.24; H, 5.36; N, 10.35.

EXAMPLE 7

1-Amino-2-[3-(3-hydroxymethylphenoxy)-propylamino]-1-cyclobutene-3,4-dione

A suspension of 1-amino-2-[3-(3-formylphenoxy)-propylamino]-1-cyclobutene-3,4-dione (2.09 g, 7.29 mmoles), piperidine (0.8 mL, 690 mg, 8.1 mmoles) and 200 mg of 10% Pd/C in 300 mL of 95% ethanol was shaken on a Parr hydrogenator at 50 psi for 4 hours. To the resultant mixture with stirring was added 8.3 mL of aqueous 1.0N HCl and 25 mL of water. The reaction mixture was filtered through diatomaceous earth and the filtrate was evaporated under reduced pressure. The solid residue was treated with acetone and allowed to stand at 0° C. for 18 hours. The mixture was filtered and the solid dried to give 1.437 g of product containing a small amount of starting aldehyde; mp=207°–212° C.

A 1.31 g sample was further purified by recrystallization from 65 mL of 95% ethanol to give 1.173 g of title compound.

Anal. Calcd for $C_{14}H_{16}N_2O_4$: C, 60.86; H, 5.84; N, 10.14. Found: C, 60.68; H, 5.76; N, 10.19.

EXAMPLE 8

1-Amino-2-[3-(3-chloromethylphenoxy)propylamino]-1-cyclobutene-3,4-dione

When 1-amino-2-[3-(3-hydroxymethyl-phenoxy)-propylamino]-1-cyclobutene-3,4-dione is treated with at least one equivalent of thionyl chloride, there is thereby produced the title compound.

EXAMPLE 9

1-Amino-2-[3-(3-benzenesulfonylmethylphenoxy)-propylamino]-1-cyclobutene-3,4-dione When a solution of 1-amino-2-[3-(3-hydroxymethyl-phenoxy)propylamino-1-cyclobutene-3,4-dione in dimethylformamide is treated with at least one equivalent of pyridine and about one equivalent of benzenesulfonyl chloride, there is thereby produced the title compound.

EXAMPLE 10

1-Amino-2-[3-(3-piperidinomethylphenoxy)-propylamino]-1-cyclobutene-3,4-dione

A suspension of 1-amino-2-[3-(3-formylphenoxy)-propylamino]-1-cyclobutene-3,4-dione (6.0 g, 21.8 mmole) in 150 mL of toluene was treated with piperidine (4.3 mL, 3.7 g, 43.6 mmole) and the mixture was heated to 65° C., and then cooled to about 30° C. Formic acid (2.2 mL of 95% aqueous formic acid containing 2.5 g formic acid, 55.4 mmole) was added. The mixture was heated to reflux temperature and the water formed was collected by azeotropic distillation. When the distillate became clear and gas evolution had ceased (about 30 minutes at reflux), the mixture was cooled and the solids were collected by filtration, washed with toluene, methanol and dried to yield 4.7 g (62.8%) of the title compound; mp=223°–228° C.

Anal. Calcd for $C_{19}H_{25}N_3O_3$: C, 66.45; H, 7.33; N, 12.23. Found: C, 66.18; H, 7.35; N, 12.17.

EXAMPLE 11

1-Amino-2-{3-(3-[1,1-diethoxymethyl]phenoxy)-propylamino}-1-cyclobutene-3,4-dione A 500 mL 3-neck flask was charged with N-[3-(3-formylphenoxy)propyl]phthalimide (15.45 g, 0.05 mole), ammonium chloride (0.55 g, 0.01 mole), triethyl orthoformate (15.1 g, 0.1 mole, 17 mL) and absolute ethanol (100 mL). The reaction was heated at reflux overnight. After about 16 hours, the reaction was cooled to 30°–35° C. Hydrazine hydrate (15.3 g, 0.26 mole, 85%) and ethanol (200 mL) were added and the reaction was reheated to reflux and held for 6 hors at this point. The thick mixture was cooled to 0°–5° C., held for 30 minutes and filtered by vacuum to remove the precipitated by-product. The filter cake was washed twice with absolute ethanol (2×100 mL) and the filtrates were combined.

A solution of 1-amino-2-butoxy-1-cyclobutene-3,4-dione (8.46 g, 0.05 mole) in methanol (200 mL) was prepared by warming on a steam bath. This solution was added to the filtrates from above containing 3-(3-[1,1-diethoxymethyl]phenoxy)propylamine and the reaction was stirred at ambient temperature.

1-Amino-2-{3-(3-[1,1-diethoxymethyl]phenoxy)-propylamino}-1-cyclobutene-3,4-dione, which precipitates during the reaction, is isolated by vacuum filtration, then is washed with ethanol and dried.

What is claimed is:

1. A compound of the formula

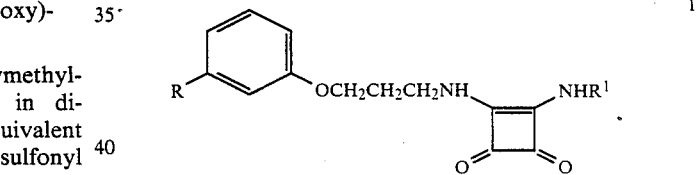

wherein $R^1$ is hydrogen or lower alkyl and R is —CHO,

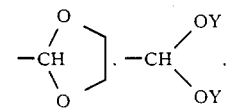

—CH$_2$OH or —CH$_2$X in which X is a conventional leaving group and Y is lower alkyl.

2. A compound of claim 1 wherein $R^1$ is hyrogen.
3. A compound of claim 2 wherein R is —CH$_2$OH.
4. A compound of claim 1 which is 1-amino-2-{3-[3-(1,3-dioxolan-2-yl)phenoxy]propylamino}-1-cyclobutene-3,4-dione.
5. A compound of claim 1 which is 1-amino-2-[3-(3-formylphenoxy)propylamino]-1-cyclobutene-3,4-dione.

* * * * *